( 12 ) United States Patent
Luebke et al.

(10) Patent No.: US 10,294,173 B2
(45) Date of Patent: May 21, 2019

(54) INTEGRATION OF A DEHYDROGENATION UNIT AND AN ALKYLATION UNIT

(71) Applicant: UOP LLC, Des Plaines, IL (US)

(72) Inventors: Charles P. Luebke, Mount Prospect, IL (US); Raul Zavala, Chicago, IL (US); Christopher D. DiGiulio, Elmhurst, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/994,996

(22) Filed: May 31, 2018

(65) Prior Publication Data

US 2019/0002370 A1   Jan. 3, 2019

Related U.S. Application Data

(60) Provisional application No. 62/527,741, filed on Jun. 30, 2017.

(51) Int. Cl.
*C07C 2/62* (2006.01)
*C07C 2/60* (2006.01)
*C07C 5/27* (2006.01)
*C07C 5/05* (2006.01)
*C07C 9/16* (2006.01)
*C07C 5/52* (2006.01)

(52) U.S. Cl.
CPC .............. *C07C 5/2729* (2013.01); *C07C 2/60* (2013.01); *C07C 2/62* (2013.01); *C07C 5/05* (2013.01); *C07C 5/52* (2013.01); *C07C 9/16* (2013.01); *C07C 2527/054* (2013.01); *C07C 2527/1206* (2013.01)

(58) Field of Classification Search
CPC ............ C07C 2/62; C07C 2/60; C07C 5/2729
USPC ....... 585/315, 316, 331, 258, 654, 734, 721, 585/723, 731, 727
See application file for complete search history.

(56) References Cited

U.S. PATENT DOCUMENTS

2002/0087040 A1* 7/2002 Marchionna .............. C07C 9/14
585/331

* cited by examiner

*Primary Examiner* — Thuan D Dang

(57) ABSTRACT

The present invention relates to the integration of an alkylation unit for use in a hydrocarbon conversion process. More specifically, the present invention relates to the integration of a dehydrogenation unit and an alkylation unit and the placement of different isomerization units located off the deisobutanizer and the debutanizer.

5 Claims, 2 Drawing Sheets

INTEGRATION OF A DEHYDROGENATION UNIT AND AN ALKYLATION UNIT

CROSS-REFERENCE TO RELATED APPLICATION

This application claims priority from Provisional Application No. 62/527,741 filed Jun. 30, 2017, the contents of which cited application are hereby incorporated by reference in its entirety.

FIELD

The present invention relates to the integration of an alkylation unit for use in a hydrocarbon conversion process. More specifically, the present invention relates to the integration of a dehydrogenation unit and an alkylation unit and the placement of different isomerization units located off the deisobutanizer and the debutanizer.

BACKGROUND

A process for the conversion of paraffins to olefins involves passing a normal paraffin stream over a highly selective catalyst, where the normal paraffin is dehydrogenated to the corresponding mono-olefin. The dehydrogenation reaction is achieved under mild operating conditions, thereby minimizing the loss of feedstock.

The typical process involves the use of a radial flow reactor where a paraffin feedstock is contacted with a dehydrogenation catalyst under reaction conditions. The typical process involves dehydrogenating linear paraffins in the $C_2$ to $C_{11}$ range to produce olefins used as monomers used in the formation of polymers, or as plasticizers, or for dehydrogenating paraffins in the $C_{10}$ to $C_{14}$ range to produce linear olefins for the production of linear alkyl benzenes (LABs), and for dehydrogenating paraffins in the $C_{12}$ to $C_{17}$ range to produce detergent alcohols or olefin sulfonates.

As an example, sulfuric acid alkylation prefers linear $C_4$ olefins as a feedstock because alkylation with n-butene and isobutane produces higher octane alkylate, as high octane alkylate is synonymous with high octane gasoline. Typically, olefins are either externally purchased or are present in internal refinery streams. Recent changes in feedstock pricing and feedstock availability have created interest in first producing the linear olefins required, followed by subsequent alkylation.

SUMMARY

In the flow scheme disclosed in the present invention, instead of separating the field butanes into nC4 and iC4, respectively, the field butanes are directly fed to the dehydrogenation unit. This results in some formation of isobutylene in addition to normal butylenes, which may in some embodiment result in marginal changes to the octane value but it has numerous, advantages including eliminates the feed deisobutanizer column (DIB), decreases the size of the alkylation reactors, decreases the size of the existing alkylation DIB, makes use of existing equipment required in the alkylation complex, minimizes the nc4 recycle, and reduces capex and utilities.

DETAILED DESCRIPTION

Butenes and butadienes are important chemical precursors for rubbers, polymers, and other materials used in common products. Isobutylene is also used in the production of alkylate, wherein the alkylate which can be used in a blending pool for gasoline.

The alkylation of $C_4$ olefins to form alkylate is performed in an alkylation process. Examples of alkylation units are sulfuric acid alkylation, HF alkylation, ionic liquid alkylation. When field butanes are fed directly to the dehydrogenation unit, there is no longer a need to use the DIB to separate the feed. Since dehydrogenation unit yields isobutane, isobutene, n-butane and n-butenes as products and everything but butane reacts in the alkylation unit, the lower butane concentration in the feed means that less butane passes through the alkylation unit unreacted Also, since there is less butane in the system, there is also less feed going to the alkylation unit DIB. The butamer size does increase since there is now a need to produce more isobutane to meet the required isobutene makeup.

Figure 1:
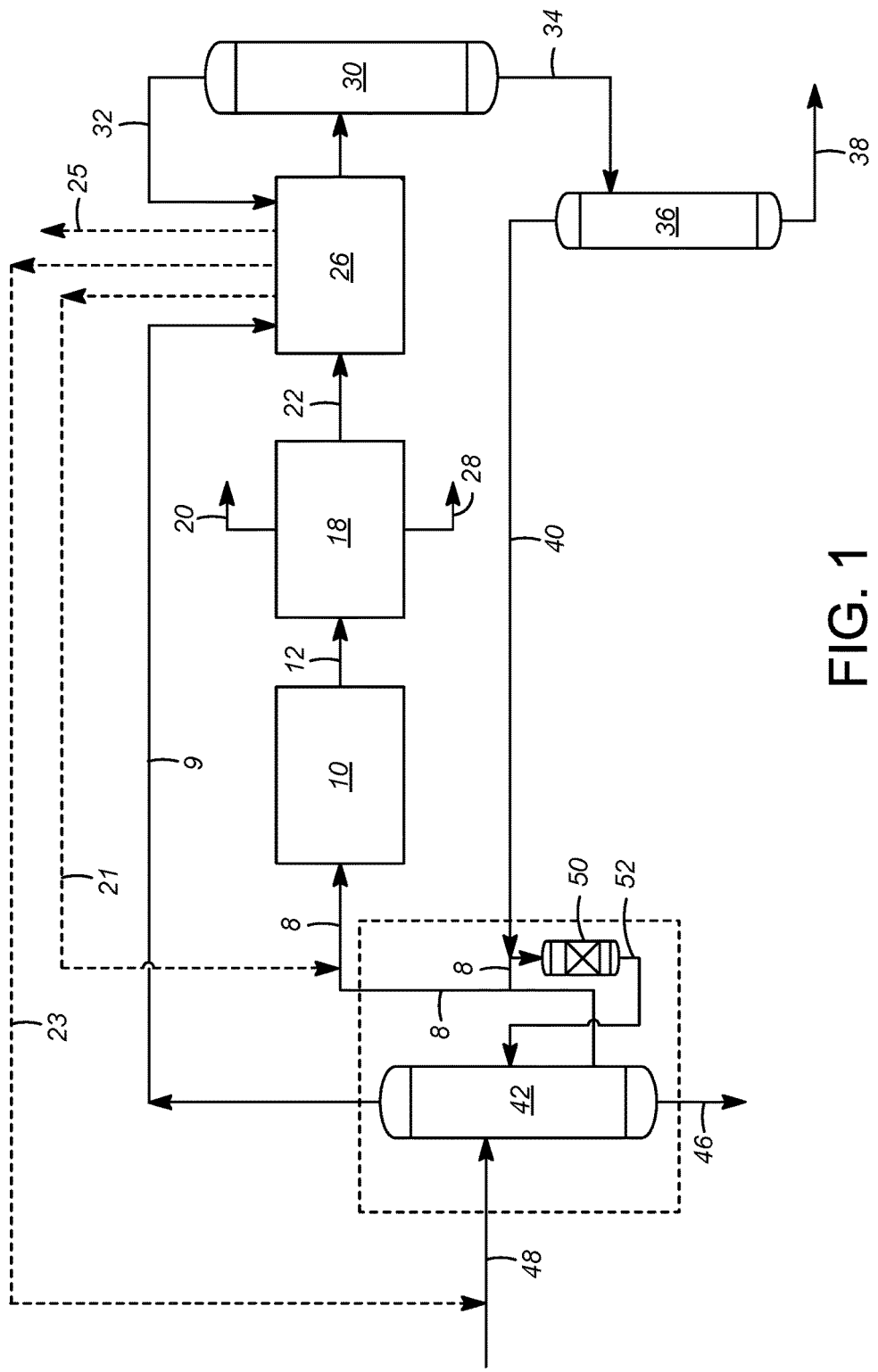
FIG. 1 illustrates the current state of the art.

The prior art, as shown in FIG. 1 illustrates passing a hydrocarbon stream 8 to a dehydrogenation unit 10 to generate a first process stream 12 comprising olefins. An overhead stream 9 is passed to an alkylation unit 26. The first process stream 12 is passed to a dehydrogenation fractionation section 18. The dehydrogenation fractionation section 18 produces an overhead stream 20 and a bottoms stream 28. The dehydrogenation fractionation section product stream 22 is passed to an alkylation zone 26 which produces an alkylate product stream 28 comprising alkylate and unreacted $C_4$ compounds which is passed to a first deisobutanizer 30.

The deisobutanizer 30 produces an overhead steam 32 which is sent back to the alkylation zone 26 and a products stream 34 which is passed to a debutanizer 36. The debutanizer 36 produces a bottoms stream 38 comprising alkylate and an overhead stream 40 which is passed to a second deisobutanizer 42. The second deisobutanizer 42 also receives butanes in stream 48 and produces an n-butane rich stream 8 that enters the dehydrogenation zone 10, a bottoms stream 46 comprising $C_{5+}$ and a side cut stream 44 which is sent to a isomerization unit 50. The isomerization unit 50 produces stream 52 which is sent back to the second deisobutanizer.

Figure 2:
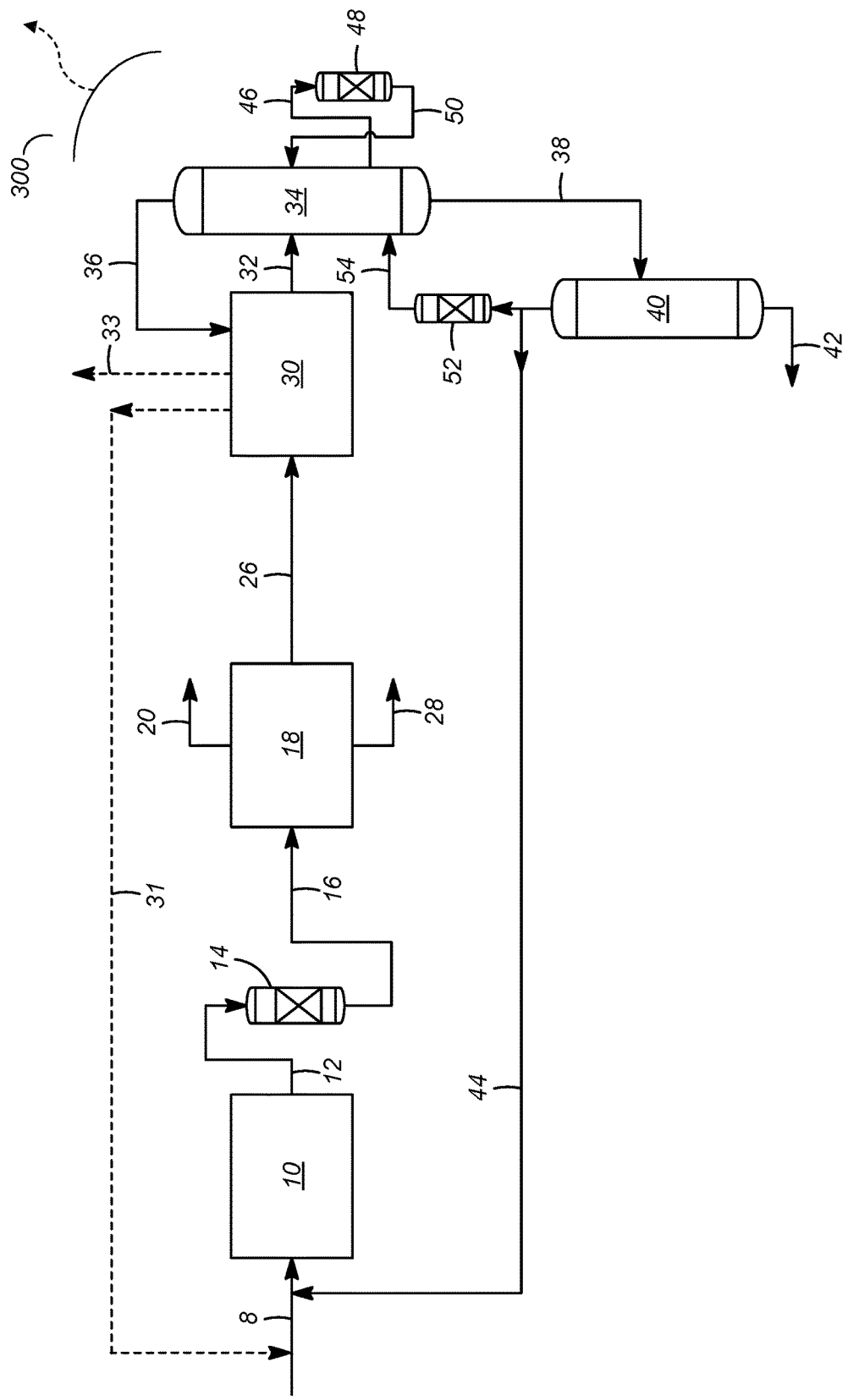
FIG. 2 illustrates the integration of a dehydrogenation unit and an alkylation unit, with the removal of one DIB and highlighting the potential location of the butane isomerization unit.

In the claimed invention illustrated in FIG. 2, there is no need for two separate di-isobutanizers. Instead there is one deisobutanizer 34, and the butanes feed 8 directly into the dehydrogenation unit 10. The dehydrogenation unit 10 produces a product stream 12 which is sent to a selective hydrogenation unit 14 to produce a product stream 16 which is sent to a dehydrogenation fractionation section 18. In some embodiments, a selective hydrogenation unit 14 may not be needed. The dehydrogenation fractionation section 18 produces an overhead stream lights 20 and a bottoms stream 28. The bottoms stream 28 is removed as needed to meet alkylation requirements. The dehydrogenation fractionation section 18 product stream 26 is passed to the alkylation zone 30. The alkylation zone 30 produces a product stream 32 which is passed to the deisobutanizer 34. A deisobutanizer bottoms stream 38 is passed to the debutanizer 40 which produces a bottoms stream 42 comprising alkylate and an overhead stream 44 which is sent back to be combined with the butanes stream 8 which is sent to the dehydrogenation unit 10. In a first embodiment, a side cut 46 from the deisobutanizer 34 is sent to an isomerization unit 48 which produces a product stream 50 which is sent back to the deisobutanizer 34. In a second embodiment, a portion of the overhead stream 44 is sent to an isomerization unit 52 which produces stream 54 which is sent back to the deisobutanizer 34. In a third embodiment, both the isomerization unit 48 and the isomerization unit 52 would remain in place, sending both streams 50 and 54 back to the deisobutanizer 34. Therefore, the invention may include the isomerization unit 48, the isomerization unit 52, or both the isomerization unit 48 and 52. The isomerization units may be bumaters.

In an exemplary embodiment, the alkylation zone 30 may comprise a depropanizer (not shown) and a $C_{3-}$ stream, comprising predominantly $C_3$ hydrocarbons, may be withdrawn in line 31 and passed back to the butanes feed 8 and subsequently passed to the dehydrogenation unit 10. Also, optionally, a $C_3$– purge stream may be taken out in line 33.

In alternative exemplary embodiment, the alkylation zone 30 may not comprise a depropanizer and a $C_{4-}$ stream, comprising predominantly $C_3$ and $C_4$ hydrocarbons, may be withdrawn in line 31 and passed back to the butanes feed 8 and subsequently passed to the dehydrogenation unit 10. Also, optionally, a $C_4$– purge stream may be taken out in line 33.

The instant invention provides flexibility to recycle the either $C_{4-}$ or $C_{3-}$ recovered from the alkylation zone 30 back to the instant process.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect. The figure shows the above categorically as 300.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein. The figure shows the above categorically as 300.

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for dehydrogenation and alkylation, comprising passing a hydrocarbon stream to a dehydrogenation unit to generate a process stream comprising olefins; passing the process stream to a selective hydrogenation unit to generate a selective hydrogenation unit product stream; passing the selective hydrogenation unit product stream to a dehydrogenation fractionation unit to generate a light stream, a heavies stream, and a dehydrogenation fractionation product stream; passing the dehydrogenation fractionation product stream to an alkylation unit to produce an alkylation unit product stream; passing the alkylation unit product stream to a deisobutanizer to generate a deisobutanizer overhead stream and a deisobutanizer bottoms stream; passing the deisobutanizer bottoms stream to a debutanizer to generate a debutanizer overhead stream and a debutanizer products stream. passing a portion of the debutanizer overhead stream to an isomerization unit to generate an isomerization unit product stream which is passed to the deisobutanizer; and passing a portion of the debutanizer overhead stream to the dehydrogenation unit. An embodiment of the invention is one, any or all of prior embodiments in this paragraph up through the first embodiment in this paragraph, further comprising passing a portion of the debutanizer overhead stream to an isomerization unit to generate an isomerization unit product stream which is passed to the deisobutanizer and passing a portion of the debutanizer overhead stream to the dehydrogenation unit. An embodiment of the invention is one, any or all of prior embodiments in this paragraph up through the first embodiment in this paragraph, further comprising passing a deisobutanizer side cut to an isomerization unit to generate an isomerization unit product stream which is passed to the deisobutanizer. An embodiment of the invention is one, any or all of prior embodiments in this paragraph up through the first embodiment in this paragraph, wherein the hydrocarbon stream comprises normal butane or isobutane or a mixture of butane and isobutane. An embodiment of the invention is one, any or all of prior embodiments in this paragraph up through the first embodiment in this paragraph, wherein the hydrocarbon stream comprises about 38% isobutanes and about 58% normal butanes. An embodiment of the invention is one, any or all of prior embodiments in this paragraph up through the first embodiment in this paragraph, wherein the isomerization unit is a butamer. An embodiment of the invention is one, any or all of prior embodiments in this paragraph up through the first embodiment in this paragraph, wherein the isomerization unit is a butamer. An embodiment of the invention is one, any or all of prior embodiments in this paragraph up through the first embodiment in this paragraph, wherein the alkylation unit is a sulfuric acid alkylation unit. An embodiment of the invention is one, any or all of prior embodiments in this paragraph up through the first embodiment in this paragraph, wherein the alkylation unit is an HF alkylation unit. An embodiment of the invention is one, any or all of prior embodiments in this paragraph up through the first embodiment in this paragraph, wherein the alkylation unit is an ionic liquid alkylation unit.

A second embodiment of the invention is a process for dehydrogenation and alkylation, comprising passing a hydrocarbon stream to a dehydrogenation unit to generate a process stream comprising olefins; passing the process stream to a selective hydrogenation unit to generate a selective hydrogenation unit product stream; passing the selective hydrogenation unit product stream to a dehydrogenation fractionation to generate a dehydrogenation fractionation product stream; passing the dehydrogenation fractionation product stream to an alkylation unit to produce an alkylation unit product stream; passing the alkylation unit product stream to a deisobutanizer to generate a deisobutanizer overhead stream and a deisobutanizer bottoms stream; passing the deisobutanizer bottoms stream to a debutanizer to generate a debutanizer overhead stream and a debutanizer products stream. Passing a portion of the debutanizer overhead stream to an isomerization unit to generate an isomerization unit product stream which is passed to the deisobutanizer; passing a portion of the debutanizer overhead stream to the dehydrogenation unit. An embodiment of the invention is one, any or all of prior embodiments in this paragraph up through the second embodiment in this paragraph, wherein the hydrocarbon stream comprises normal butane or isobutane or a mixture of butane and isobutane. An embodiment of the invention is one, any or all of prior embodiments in this paragraph up through the second embodiment in this paragraph, wherein the hydrocarbon stream comprises about 38% isobutanes and about 58% normal butanes. An embodiment of the invention is one, any or all of prior embodiments in this paragraph up through the second embodiment in this paragraph, wherein the isomerization unit is a butamer. An embodiment of the invention is one, any or all of prior embodiments in this paragraph up through the second embodiment in this paragraph, wherein the alkylation unit is a sulfuric acid alkylation unit. An embodiment of the invention is one, any or all of prior embodiments in this paragraph up through the second embodiment in this paragraph, wherein the alkylation unit is an HF alkylation unit. An embodiment of the invention is one, any or all of prior embodiments in this paragraph up through the second embodiment in this paragraph, wherein the alkylation unit is an ionic liquid alkylation unit.

A third embodiment of the invention is a process for dehydrogenation and alkylation, comprising passing a hydrocarbon stream to a dehydrogenation unit to generate a process stream comprising olefins; passing the process stream to a selective hydrogenation unit to generate a selective hydrogenation unit product stream; passing the selective hydrogenation unit product stream to a dehydrogenation fractionation to generate a dehydrogenation fractionation product stream; passing the dehydrogenation fractionation product stream to an alkylation unit to produce an alkylation unit product stream; passing the alkylation unit product stream to a deisobutanizer to generate a deisobutanizer overhead stream and a deisobutanizer bottoms stream; passing the deisobutanizer bottoms stream to a debutanizer to generate a debutanizer overhead stream and a debutanizer products stream; passing a deisobutanizer side cut to an isomerization unit to generate an isomerization unit product stream which is passed to the deisobutanizer; passing a portion of the debutanizer overhead stream to an isomerization unit to generate an isomerization unit product stream which is passed to the deisobutanizer; and passing a portion of the debutanizer overhead stream to the dehydrogenation unit. An embodiment of the invention is one, any or all of prior embodiments in this paragraph up through the third embodiment in this paragraph, wherein the hydrocarbon stream comprises normal butane or isobutane or a mixture of butane and isobutane. An embodiment of the invention is one, any or all of prior embodiments in this paragraph up through the third embodiment in this paragraph, wherein the hydrocarbon stream comprises about 38% isobutanes and about 58% normal butanes. An embodiment of the invention is one, any or all of prior embodiments in this paragraph up through the third embodiment in this paragraph, wherein the isomerization unit is a butamer. An embodiment of the invention is one, any or all of prior embodiments in this paragraph up through the third embodiment in this paragraph, wherein the alkylation unit is a sulfuric acid alkylation unit. An embodiment of the invention is one, any or all of prior embodiments in this paragraph up through the third embodiment in this paragraph, wherein the alkylation unit is an HF alkylation unit. An embodiment of the invention is one, any or all of prior embodiments in this paragraph up through the third embodiment in this paragraph, wherein the alkylation unit is an ionic liquid alkylation unit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims. In the foregoing, all temperatures are set forth in degrees Celsius and, all parts and percentages are by weight, unless otherwise indicated.

The invention claimed is:

1. A process for dehydrogenation and alkylation, comprising:
    passing a field butane stream comprising about 38% isobutane and about 58% n-butane directly to a dehydrogenation unit to generate a process stream comprising isobutane, isobutene, n-butane and n-butenes;
    passing the process stream to a selective hydrogenation unit to generate a selective hydrogenation unit product stream comprising isobutane, isobutene, n-butane and n-butenes;
    passing the selective hydrogenation unit product stream to a dehydrogenation fractionation unit to generate a light stream, a heavies stream, and a dehydrogenation fractionation product stream;
    passing the dehydrogenation fractionation product stream to an alkylation unit to produce an alkylation unit product stream comprising alkylate;
    passing the alkylation unit product stream to a deisobutanizer to generate a deisobutanizer overhead stream and a deisobutanizer bottoms stream;
    passing the deisobutanizer bottoms stream to a debutanizer to generate a debutanizer overhead stream and a debutanizer alkylate products stream;
    passing a deisobutanizer side cut to a first isomerization unit to generate a first isomerization unit product stream with an increase of isobutane which is passed to the deisobutanizer;
    passing a portion of the debutanizer overhead stream to a second isomerization unit to generate a second isomerization unit product stream with an increase of isobutane which is passed to the deisobutanizer; and
    passing a portion of the debutanizer overhead stream to the dehydrogenation unit.

2. The process of claim 1, wherein the alkylation unit is a sulfuric acid alkylation unit.

3. The process of claim 1, wherein the alkylation unit is an HF alkylation unit.

4. The process of claim 1, wherein the alkylation unit is an ionic liquid alkylation unit.

5. The process of claim 1, further comprising at least one of:
- sensing at least one parameter of the process and generating a signal or data from the sensing;
- generating and transmitting a signal; or
- generating and transmitting data.

* * * * *